US005935586A

United States Patent [19]

De Lacharriere et al.

[11] Patent Number: 5,935,586

[45] Date of Patent: Aug. 10, 1999

[54] THERAPEUTIC/COSMETIC COMPOSITIONS COMPRISING CGRP ANTAGONISTS FOR TREATING DISEASE STATES OF THE SKIN

[75] Inventors: Olivier De Lacharriere, Paris; Lionel Breton, Versailles, both of France

[73] Assignee: Societe L'Oreal S.A., Paris, France

[21] Appl. No.: 08/620,805

[22] Filed: Mar. 28, 1996

[30] Foreign Application Priority Data

Mar. 28, 1995 [FR] France .................................. 95 03627

[51] Int. Cl.[6] .............................. A61K 7/00; A61K 7/48; A61K 39/00; A61K 39/395

[52] U.S. Cl. ......................... 424/401; 424/450; 424/451; 424/490; 424/139.1; 424/198.1; 424/130.1; 514/2

[58] Field of Search ................................ 424/401, 130.1, 424/450, 451, 490, 139.1, 198.1; 514/2

[56] References Cited

U.S. PATENT DOCUMENTS 5,445,823 8/1995 Hall et al. .............................. 424/401

FOREIGN PATENT DOCUMENTS

93/21911 11/1993 WIPO .

OTHER PUBLICATIONS

Lundbad et al. 1987 Allergy 42 (1) pp. 20–25, Jan. 1987.

Vaalasti et al. 1989 Br. J Dermatology 120 (5) pp. 619–623, May 1989.

Neuroscience, vol. 48, No. 4, Jun. 1992, pp. 963–968, T.L. Buckley, et al., 'The Partial Inhibition of Inflammatory Responses Induced by a Capsaicin Using the Fab Fragment of a Selective Calcitonin Gene–Related Peptide Antiserum in Rabbit Skin.'

British Journal of Pharmacology, vol. 110, No. 2, 1993, pp. 772–776, K. Jane Escott, et al., 'Effect of Calcitonin Gene–Related Peptide Antagonist (CGRP 8–37) on Skin Vasodilatation and Oedema Induced by Stimulation of the Rat Saphenous Nerve.'

British Journal of Pharmacology, vol. 104, No. 3, Nov. 1991, pp. 738–742, S.R. Hughes, et al., 'A Calcitonin Gene–Related Peptide (CGRP) Antagonist (CGRP 8–37) Inhibits Microvascular Responses Induced by CGRP and Capsaicin in Skin.'

Neuroscience Letters, vol. 102, No. 2.3, Jul. 31, 1989, pp. 257–260, S.M. Louis, et al., 'Antibodies to Calcitonin Gene–Related Peptide Reduce Inflammation Induced by Topical Mustard Oil But Not That Due To Carrageenin in the Rat.'

Hua et al. 1993 J Neurosci 13 (5) pp. 1947–1953, May 1, 1993.

Ostlere et al. 1995 Clinical and Experimental Dermatology 20 (nov) pp. 462–467, Nov. 1, 1995.

Peskar et al. 1993 Eur J Pharmacology 250 pp. 201–203, Jan. 1, 1993.

Shaw et al. 1992 Br J Pharmacol 106 pp. 196–198, Jan. 1, 1992.

Bartho et al. 1991 Neuroscience Letters 129 pp. 156–159, Jan. 1, 1991.

Brain et al 1986 J Invest Dermatol 87 pp. 533–536, Jan. 1, 1986.

Fuller et al. 1987 Br J Pharmacol 92 pp. 781–788, Jan. 1, 1987.

Herbert et al. 1994 Br J Pharmacol 111 pp. 681–686, Jan. 1, 1994.

Tan et al. 1995 Clinical Science 89 pp. 565–5733, Dec. 1, 1995.

Wallengren et al. 1987 Eur J Pharmacol 143 pp. 267–273, Nov. 10, 1987.

*Primary Examiner*—Frank C. Eisenschenk
*Assistant Examiner*—Mary K Zeman
*Attorney, Agent, or Firm*—Burns, Doane, Swecker & Mathis, L.L.P.

[57] ABSTRACT

Lichens, prurigos, pruriginous toxidermias and/or severe pruritus afflicting a mammalian, notably human patient, are therapeutically treated by administrating to such patient a therapeutically/cosmetically effective amount of at least one CGRP antagonist, advantageously in combinatory immixture with at least one antagonist of a neuropeptide other than CGRP, e.g., a substance P antagonist, and/or at least one inflammation mediator antagonist.

19 Claims, No Drawings

THERAPEUTIC/COSMETIC COMPOSITIONS COMPRISING CGRP ANTAGONISTS FOR TREATING DISEASE STATES OF THE SKIN

CROSS-REFERENCE TO COMPANION APPLICATIONS

Copending applications Ser. No. 08/592,529, filed Jan. 26, 1996, and Ser. No. 08/623,576 and Ser. No. 08/620,806, both filed concurrently herewith, and each assigned to the assignee hereof.

BACKGROUND OF THE INVENTION

1. Technical Field of the Invention

The present invention relates to the formulation of an antagonist of CGRP (peptide derived from the calcitonin gene: Calcitonin Gene Related Peptide, or "CGRP") into cosmetic/pharmaceutical/dermatological compositions, in particular for topical application, for the treatment of certain disease states of the skin.

More especially, this invention relates to the topical, ingestible (oral) or injectable (enteral) treatment of lichens, in particular flat lichens and pigmentary lichens; prurigos and in particular actinic prurigo, Besnier's prurigo or Hebra's prurigo or strophulus or Hyde's prurigo; pruriginous toxidermias and severe pruritus, notably those afflicting blood dialysis patients and AIDS patients, and cholestatic or biliary pruritus. Pruriginous toxidermias occur in particular after absorption of medicaments; these disease states are very different from urticaria and do not entail any contact reaction.

2. Description of the Prior Art

It is known to this art to treat flat lichens and pigmentary lichens using local corticoids or those from PUVA therapy. Although, admittedly, corticoids are very effective in alleviating the symptoms, they have side effects which are often very deleterious, such as atrophies, especially mycotic or bacterial infections. PUVA therapy is the local irradiation of diseased skin with UVA radiation, after absorption of a photosensitizing substance (psoralen). This technique presents the serious drawback of a photoaging which is apt to produce skin cancers. Furthermore, this treatment is not ambulatory, requiring the patient to regularly visit a specialist center throughout the duration of the treatment, which is very restricting and limits his or her professional activity.

Prurigos are also treated by local corticoids, PUVA therapy or thalidomide. Local corticoids and PUVA therapy present the above drawbacks. Thalidomide presents the major disadvantage of being teratogenic, which prohibits its use in pregnant women. Furthermore, its very tightly controlled prescription (restricted to hospital doctors) limits its use.

Pruriginous toxidermias are currently treated by means of local corticoids and/or antihistamines: such treatment thus presents the same drawbacks as those indicated above.

Severe pruritus is also treated with local corticoids, with the same drawbacks as those indicated above.

Thus, serious need continues to exist in this art for a treatment of the aforesaid skin afflictions which does not have the above drawbacks/disadvantages.

SUMMARY OF THE INVENTION

Briefly, the present invention features the formulation, in a cosmetically, pharmaceutically and/or dermatologically acceptable medium, of one or more CGRP antagonists, for the effective treatment of certain diseases states of the skin, while at the same time avoiding or conspicuously ameliorating the aforesaid disadvantages and drawbacks to date characterizing the state of this art.

DETAILED DESCRIPTION OF BEST MODE AND SPECIFIC/PREFERRED EMBODIMENTS OF THE INVENTION

More particularly according to the present invention, it will be appreciated that CGRP is a polypeptide chemical entity produced and released by a nerve ending. CGRP is involved, in particular, in respiratory and inflammatory diseases, in allergic diseases and in certain dermatological diseases such as eczema and prurigo.

However, to date it has not been envisaged to treat lichens, prurigos, pruriginous toxidermias and severe pruritus with CGRP antagonists.

Accordingly, the present invention features the use of at least one CGRP antagonist in and/or for the formulation of a cosmetic, pharmaceutical and/or dermatological composition for treating lichens, prurigos, pruriginous toxidermias and severe pruritus.

By "CGRP antagonist" is intended any molecule, whether organic or inorganic, which is capable of effecting inhibition of the receptor binding of CGRP or of effecting inhibition of the synthesis and/or release of CGRP by sensitive nerve fibers.

In order for a chemical species to be recognized as a CGRP antagonist, it must in particular satisfy the following characteristic: have a CGRP antagonist pharmacological activity, i.e., induce a coherent pharmacological response, in particular in one of the following tests:

(a) the antagonist species must reduce the vasodilation induced by capsaicin and/or (b) the antagonist species must induce an inhibition of the release of CGRP by sensitive nerve fibers and/or (c) the antagonist species must induce an inhibition of the contraction of vas deferens smooth muscle induced by CGRP.

In addition, the antagonist may have an affinity for the CGRP receptors.

CGRP 8-37, an anti-CGRP antibody, is suitable for use according to the invention, for example as CGRP antagonist.

In the compositions according to the invention, the CGRP antagonist is preferably employed in an amount ranging from 0.000001% to 10% by weight relative to the total weight of the composition, and in particular in an amount ranging from 0.0001% to 5% by weight relative to the total weight of the composition.

The CGRP antagonist may advantageously be combined with one or more antagonists of another neuropeptide such as substance P antagonists and/or one or more inflammation mediator antagonists such as histamine antagonists, interleukin 1 (IL1) antagonists and Tumor Necrosis Factor alpha (TNF $\alpha$) antagonists.

Thus, the present invention also features cosmetic/pharmaceutical/dermatological compositions, comprising, in a cosmetically, pharmaceutically and/or dermatologically acceptable medium (vehicle, diluent or carrier), at least one CGRP antagonist and at least one antagonist of another neuropeptide and/or at least one inflammation mediator antagonist.

Similarly, this invention also features cosmetic/pharmaceutical/dermatological compositions for treating lichens and pruritus, comprising, in a cosmetically, pharmaceutically and/or dermatologically acceptable medium, at least one CGRP antagonist and at least one antagonist of another neuropeptide and/or at least one inflammation mediator antagonist.

The antagonist of a neuropeptide other than CGRP is preferably a substance P antagonist.

Substance P is a polypeptide chemical species produced and released by a nerve ending. It is a member of the family of tachykinins which originate from free nerve endings in the epidermis and the dermis. Substance P is involved, in particular, in the transmission of pain and in central nervous system disorders such as anxiety and schizophrenia, in respiratory and inflammatory diseases, in gastrointestinal diseases, in rheumatic diseases and in certain dermatological diseases such as eczema, psoriasis, urticaria and contact dermatitis.

Exemplary substance P antagonists according to the invention include any active species of organic or inorganic origin that elicits an inhibition of the receptor binding of substance P or an inhibition of the synthesis and/or release of substance P by sensitive nerve fibers.

For a chemical entity to be recognized as a substance P antagonist, it must satisfy the following characteristics:

(a') it must have a selective affinity for the tachykinin NK1 receptors and/or (b') it must have a substance P antagonist pharmacological activity, namely, induce a coherent pharmacological response, in particular in one of the following two tests:

(i) the antagonist species must decrease the extravasation of the plasma across the vascular wall induced by capsaicin or by antidromic nerve stimulation, or alternatively, (ii) the antagonist species must elecit an inhibition of the contraction of smooth muscles induced by the administration of substance P.

The substance P antagonist is preferably a substance P receptor antagonist.

The substance P receptor antagonist may be a peptide or a non-peptide derivative containing a hetero atom, and, advantageously, a compound comprising a heterocycle or a heteroatom bonded directly or indirectly to a benzene ring.

Sendide and spantide II are exemplary substance P receptor antagonist peptides.

Peptides which are well suited consistent with this invention are those described, for example, in U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569 and GB-A-2,216,529.

The non-peptide substance P receptor antagonists which are suitable according to the invention include, in particular, heterocyclic compounds, in particular sulfur-containing, nitrogen-containing or oxygen-containing heterocyclic compounds or compounds comprising a nitrogen atom bonded directly or indirectly to a benzene ring.

Exemplary heterocyclic compounds according to the invention are those described in EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545,478, EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997. In particular, the compound comprising at least one nitrogen-containing heterocycle is advantageously a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

Exemplary compounds containing a nitrogen atom bonded directly or indirectly to a benzene ring include those described in EP-A-522,808 and WO-A-93/01165.

And exemplary inflammation mediator antagonists according to the invention include diethylenediamine derivatives such as cinnarizine and cyclizine; aminopropane derivatives (dexchlorpheniramine, triprolidine); phenothiazine derivatives (alimemazine, promethazine); auranofin; lisophyline; A802715; sulfasalazine; cetirizine HCl; loratidine; esbatine; setastine HCl.

By way of example, the substance P antagonists and the inflammation mediator antagonists may be formulated in an amount constituting from 0.000001% to 10% of the total weight of the composition and, preferably, from 0.0001% to 5%.

The compositions of the invention may be administered either via a local route, namely, topically or by subcutaneous and/or intradermal injection, or via a systemic or general route, namely, orally and/or by intramuscular injection.

The present invention also features the cosmetic, pharmaceutical and/or dermatological treatment of lichens, prurigos, pruriginous toxidermias and/or severe pruritus, comprising topically applying a composition containing at least one CGRP antagonist in a cosmetically, pharmaceutically and/or dermatologically acceptable medium to the skin, to the scalp and/or to the mucous membranes.

The compositions of the invention intended for topical application include a cosmetically, pharmaceutically or dermatologically acceptable medium, i.e., a vehicle, diluent or carrier which is compatible with the skin, the nails, the mucous membranes, tissues and the hair. The compositions comprising the CGRP antagonist may be applied topically to the face, the neck, the hair, the mucous membranes and the nails, major folds or any other body skin region.

The compositions according to the invention may comprise all pharmaceutical forms normally utilized according to the route of administration (injection, oral or topical route).

For topical applications, the subject compositions may be formulated into any pharmaceutical form normally employed for such an application, in particular in the form of aqueous, aqueous/alcoholic or oily solutions, dispersions of lotion or serum type, aqueous, anhydrous or lipophilic gels, emulsions of liquid or semi-liquid consistency of the milk type, obtained by dispersion of a fatty phase in an aqueous phase (O/W) or conversely (W/O), suspensions or emulsions of runny, semi-solid or solid consistency of the cream or gel type, or alternatively microemulsions, microcapsules, microparticles, or vesicle dispersions of ionic and/or nonionic type. These compositions are formulated according to conventional techniques.

They may also be used for the hair in the form of aqueous, alcoholic or aqueous/alcoholic solutions, or in the form of creams, gels, emulsions or foams or alternatively in the form of aerosol compositions also containing a propellant under pressure.

The injectable compositions may be formulated as an aqueous or oily lotion, or in the form of a serum.

The compositions for oral administration may be formulated as wafer capsules, gelatin capsules, syrups or tablets.

The amounts of the various constituents of the compositions according to the invention are those conventionally used in the fields under consideration.

These compositions constitute, in particular, protective, treatment or care creams for the face, for the hands, for the feet, for the major anatomical folds or for the body, body milks for protection or care, lotions, gels or foams for care of the skin and the mucous membranes, such as cleansing or disinfecting lotions, compositions for the bath, or compositions containing a bactericidal agent.

The subject compositions may also be formulated as solid preparations constituting soaps or cleansing bars.

The cosmetic treatments according to the invention may be carried out, in particular, by applying the cosmetic or hygienic compositions as described above, according to the usual techniques for administering these compositions. For example: application of creams, gels, sera, lotions and milks to the skin, the scalp and/or the mucous membranes.

When the compositions of the invention are formulated as an emulsion, the proportion of the fatty phase advantageously ranges from 5% to 80% by weight, and preferably from 5% to 50% by weight, relative to the total weight of the composition. The oils, the emulsifying agents and the coemulsifying agents employed in the compositions in emulsion form are selected from among those used conventionally in the cosmetics field. The emulsifying agent and the coemulsifying agent are advantageously present in the compositions, in a proportion ranging from 0.3% to 30% by weight, and preferably from 0.5 to 20% by weight, relative to the total weight of the composition. The emulsion may also contain lipid vesicles.

When the compositions of the invention comprise an oily gel or solution, the fatty phase may constitute more than 90% of the total weight of the composition.

In a known manner, the cosmetic, pharmaceutical or dermatological compositions of the invention may also contain additives and adjuvants common in such fields, such as hydrophilic or lipophilic gelling agents, hydrophilic or lipophilic active agents, preservatives, antioxidants, solvents, fragrances, fillers, sunscreens, bactericides, odor absorbers and dyestuffs and colorants. The amounts of these various additives and adjuvants are those used conventionally in the fields under consideration and range, for example, from 0.01% to 20% of the total weight of the composition. Depending on their particular nature, these additives and adjuvants may be introduced into the fatty phase, into the aqueous phase and/or into lipid spherules.

Exemplary oils which are suitable for the compositions of the invention include mineral oils (liquid petrolatum), plant oils (liquid fraction of karite butter and sunflower oil), animal oils (perhydrosqualene), synthetic oils (purcellin oil), silicone oils (cyclomethicone) and fluoro oils (perfluoropolyethers). Fatty alcohols, fatty acids (stearic acid) and waxes (paraffin wax, carnauba wax or beeswax) may also be used as fats.

Exemplary emulsifying agents according to the invention include glyceryl stearate, PPG-3 myristyl ether and cetyldimethicone copolyol.

Exemplary solvents according to the invention include the lower alcohols, in particular ethanol and isopropanol, and propylene glycol.

Exemplary hydrophilic gelling agents which are suitable include carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, representative thereof are the modified clays such as bentones, fatty acid metal salts such as aluminum stearates and hydrophobic silica, or alternatively ethylcellulose and polyethylene.

Exemplary hydrophilic active agents which may be incorporated include proteins or protein hydrolysates, amino acids, polyols, urea, allantoin, sugars and sugar derivatives, water-soluble vitamins, starch and plant extracts, in particular Aloe vera extracts.

And exemplary lipophilic active agents include retinol (vitamin A) and derivatives thereof, tocopherol (vitamin E) and derivatives thereof, essential fatty acids, ceramides and essential oils.

It is also intended, inter alia, to combine the CGRP antagonists with active agents destined, in particular, for preventing and/or treating skin complaints, conditions and afflictions. Exemplary of these active agents are:

(1) Agents which modify cutaneous differentiation and/or proliferation and/or pigmentation such as retinoic acid and isomers thereof, retinol and esters thereof, vitamin D and derivatives thereof, estrogens such as estradiol, kojic acid or hydroquinone;

(2) Antibacterial agents such as clindamycin phosphate, erythromycin or antibiotics from the tetracycline family;

(3) Antiparasitic agents, in particular metronidazole, crotamiton or pyrethroids;

(4) Antifungal agents, in particular compounds of the imidazole family such as econazole, ketoconazole or miconazole or salts thereof, polyene compounds such as amphotericin B, compounds of the allylamine family, such as terbinafine, or alternatively octopirox;

(5) Steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;

(6) Anaesthetic agents such as lidocaine hydrochloride and derivatives thereof;

(7) Antipruriginous agents such as thenaldine, trimeprazine or cyproheptadine;

(8) Antiviral agents such as acyclovir;

(9) Keratolytic agents such as alpha- and beta-hydroxycarboxylic acids or beta-ketocarboxylic acids, salts, amides or esters thereof and more particularly hydroxy acids such as glycolic acid, lactic acid, salicylic acid, citric acid and fruit acids in general, and 5-n-octanoylsalicylic acid;

(10) Anti-free-radical agents such as alpha-tocopherol or esters thereof, superoxide dismutases, certain metal-chelating agents or ascorbic acid and esters thereof;

(11) Antiseborrhoeic agents such as progesterone;

(12) Antidandruff agents such as octopirox or zinc pyrithione;

(13) Antiacne agents such as retinoic acid or benzoyl peroxide.

In order to further illustrate the present invention and the advantages thereof, the following specific examples are given, it being understood that same are intended only as illustrative and in nowise limitative.

In said examples to follow, all parts and percentages are given by weight.

EXAMPLE 1

Disinfecting Lotion for the Face or the Mucous Membranes:

| | |
|---|---|
| CGRP 8-37 | 0.50 |
| Antioxidant | 0.05 |
| Isopropanol | 40.00 |
| Preservative | 0.30 |
| Water qs | 100%. |

This composition is useful both for treating flat lichens or pigmentary lichens, as well as pruriginous toxidermias.

EXAMPLE 2

Facial or Body Gel for Treating Flat Lichens:

| | |
|---|---|
| Hydroxypropylcellulose (Klucel H marketed by Hercules) | 1.00 |
| CGRP 8-37 | 0.0001 |
| Salicylic acid | 1.00 |
| Antioxidant | 0.05 |
| Isopropanol | 40.00 |
| Preservative | 0.30 |
| Water qs | 100% |

EXAMPLE 3

Cream (oil-in-water emulsion) for Treating Severe Pruritus:

| | |
|---|---|
| Anti-CGRP antibody | 0.05 |
| Glyceryl stearate | 2.00 |
| Lactic acid/acetic acid | 1.00 |
| Polysorbate 60 (Tween 60 marketed by ICI) | 1.00 |
| Stearic acid | 1.40 |
| Triethanolamine | 0.70 |
| Carbomer | 0.40 |
| Silicone-containing oil | 12.00 |
| Perhydrosqualene | 12.00 |
| Antioxidant | 0.05 |
| Fragrance | 0.5 |
| Preservative | 0.30 |
| Water qs | 100% |

EXAMPLE 4

Gel:

The formulation of this example was identical to that of Example 3, except that it also contained 0.3% of sendide.

EXAMPLE 5

Gel for Treating Lichens:

| | |
|---|---|
| Sendide | 1.00 |
| Anti-CGRP antibody | 0.10 |
| Hydroxypropylcellulose (Klucel H) | 1.00 |
| Antioxidant | 0.05 |
| Isopropanol | 40.00 |
| Preservative | 0.30 |
| Water qs | 100% |

EXAMPLE 6

Cream (oil-in-water emulsion) for Anal Pruritus:

| | |
|---|---|
| Anti-CGRP antibody | 2.00 |
| Cetyldimethicone copolyol | 2.50 |
| NaCl | 0.60 |
| NaOH qs | pH = 5 |

-continued

| | |
|---|---|
| Cyclomethiccne | 18.00 |
| PPG-3 myristyl ether | 6.00 |
| Glycerine | 3.00 |
| Preservative | 0.20 |
| Water qs | 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for topical treatment of at least one condition selected from the group consisting of lichens, prurigos, pruriginous toxidermias and severe pruritus afflicting a mammalian subject, comprising administering to said subject, for such period of time as is required to elicit the desired therapeutic response, a therapeutically or cosmetically effective amount of at least one CGRP antagonist.

2. The method as defined by claim 1, said at least one CGRP antagonist comprising CGRP 8-37 or an anti-CGRP antibody.

3. The method as defined by claim 1, comprising topically applying said at least one CGRP antagonist to at least one of the following: the skin, scalp and mucous membranes of a human patient.

4. The method as defined by claim 1, comprising treating lichens afflicting a human patient.

5. The method as defined by claim 1, comprising treating prurigo afflicting a human patient.

6. The method as defined by claim 1, comprising treating pruriginous toxidermia afflicting a human patient.

7. The method as defined by claim 1, comprising treating severe pruritus afflicting a human patient.

8. The method as defined by claim 1, comprising further administering to said mammalian subject a therapeutically or cosmetically effective amount of another compound selected from the group consisting of at least one antagonist of a neuropeptide other than CGRP and at least one inflammation mediator antagonist.

9. The method as defined by claim 1, comprising further administering to said mammalian subject a therapeutically or cosmetically effective amount of at least one other compound selected from the group consisting of an antibacterial agent, antiparasitic agent, antifungal agent, anti-inflammatory agent, anti-pruriginous agent, anaesthetic, antiviral agent, keratolytic agent, anti-free-radical agent, anti-seborrhoeic agent, anti-dandruff agent, antiacne agent and an active agent which modifies at least one of cutaneous differentiation, proliferation and pigmentation.

10. The method as defined by claim 8, comprising further administering to said mammalian subject at least one other compound selected from the group consisting of substance P antagonist, a histamine antagonist, an interleukin 1 antagonist and a TNF $\alpha$ antagonist.

11. The method as defined by claim 1, comprising further administering to said mammalian subject at least one other compound selected from the group consisting of a protein or protein hydrolysate, amino acid, polyol, allantoin, urea, sugar or sugar derivative, vitamin, starch, plant extract, essential fatty acid, ceramide, essential oil and hydroxy acid.

12. The method as defined by claim 1, wherein said at least one CGRP antagonist contained in a composition which is in the form of a composition selected from the group consisting of a solution, emulsion, microemulsion, cream, milk, foam, gel, serum, aerosol, lotion, dispersion, microcapsule containing composition, vesicle containing composition, and microparticle containing composition.

13. The method as defined by claim 1, said at least one CGRP antagonist comprised in a form selected from the group consisting of gelatin capsules, a syrup, a soap and a cleansing bar.

14. The method as defined by claim 1, which comprises administration of a composition which comprises an amount of at least one CGRP antagonist ranging from about 0.000001% to 10% by weight thereof.

15. The method of claim 14, wherein the amount of said at least one CGRP antagonist ranges from about 0.0001 to 5% by weight thereof.

16. The method of claim 1, wherein said at least one CGRP antagonist is a chemical compound having CGRP antagonistic pharmacological activity.

17. The method of claim 1, wherein said at least one CGRP antagonist exhibits a pharmacological response in at least one of the following tests:

(i) the antagonist reduces vasodilation induced by capsaicin;

(ii) the antagonist inhibits the release of CGRP by sensitive nerve fibers; and (iii) The antagonist inhibits the contraction of vas deferens smooth muscle induced by CGRP.

18. The method of claim 17, wherein said CGRP antagonist specifically binds a CGRP receptor.

19. The method of claim 1, wherein such treatment alleviates the itching associated with said condition.

* * * * *

UNITED STATES PATENT AND TRADEMARK OFFICE

CERTIFICATE OF CORRECTION

PATENT NO. : 5,935,586

DATED : August 10, 1999

INVENTOR(S) : Olivier DE LACHARRIERE et al.

It is certified that error appears in the above-identified patent and that said Letters Patent is hereby corrected as shown below:

Column 2, line 38, please change "induce an" to --reduce--.

Signed and Sealed this

Seventeenth Day of October, 2000

Attest:

Q. TODD DICKINSON

*Attesting Officer*

*Director of Patents and Trademarks*